(12) United States Patent
Sierwald et al.

(10) Patent No.: US 9,036,768 B2
(45) Date of Patent: May 19, 2015

(54) METHOD, ARRANGEMENT, AND COMPUTER PROGRAM PRODUCT FOR EFFICIENT PRODUCTION OF TOMOGRAPHIC IMAGES

(71) Applicant: Eigenor Oy, Sodankyla (FI)

(72) Inventors: Jorn Sierwald, Kiel (DE); Markku Markkanen, Sodankyla (FI); Max Salmi, Helsinki (FI); Pauli Sundberg, Helsinki (FI)

(*) Notice: Subject to any disclaimer, the term of this patent is extended or adjusted under 35 U.S.C. 154(b) by 108 days.

(21) Appl. No.: 13/800,297

(22) Filed: Mar. 13, 2013

(65) Prior Publication Data

US 2014/0072094 A1 Mar. 13, 2014

(30) Foreign Application Priority Data

Mar. 22, 2012 (FI) ..................................... 20125327

(51) Int. Cl.
G06T 11/20 (2006.01)
G06T 11/00 (2006.01)
A61B 6/03 (2006.01)

(52) U.S. Cl.
CPC ............. *G06T 11/206* (2013.01); *G06T 11/006* (2013.01); *G06T 2211/424* (2013.01); *A61B 6/03* (2013.01)

(58) Field of Classification Search
CPC ...................................................... A61B 6/032
USPC ............................................... 378/4–20, 901
See application file for complete search history.

(56) References Cited

U.S. PATENT DOCUMENTS

| | | | |
|---|---|---|---|
| 6,507,633 B1 | 1/2003 | Elbakri et al. | |
| 8,335,358 B2 * | 12/2012 | Kalke | 382/128 |
| 8,374,309 B2 * | 2/2013 | Donath et al. | 378/19 |
| 2013/0051516 A1 * | 2/2013 | Yang et al. | 378/4 |

FOREIGN PATENT DOCUMENTS

FI 20030256 A 8/2004

OTHER PUBLICATIONS

Bedini et al. A mixed-annealing algorithm for edge preserving image ECLA A61 B 6/03 reconstruction using a limited number of projections, Signal Processing 1993, vol. 32, No. 3 pp. 397-40B, ISSN 0165-16B4 abstract, chapter 1-chapter 5, paragraph 1, Cited in Finnish Search Report.

(Continued)

*Primary Examiner* — Hoon Song (57) ABSTRACT

A method is provided for constructing a tomographic reconstruction through the application of statistical inversion. Unknowns associated with points of a reconstruction grid are represented with components of a vector-valued variable. A next version of the vector-valued variable is repeatedly created by drawing for each component a value from a conditional distribution. The components of a so generated version of the vector-valued variable are used as the tomographic reconstruction. The components are divided into sets, so that components in a set represent unknowns associated with mutually independent points of the reconstruction grid, or into independent collections. For at least two components of a set or at least two collections, the drawing of values from a conditional distribution is performed in parallel in a computer-implemented process.

20 Claims, 5 Drawing Sheets

(56) References Cited

OTHER PUBLICATIONS

Geman et al. "Stochastic Relaxation, Gibbs Distributions, and the Bayesian Restoration of images". IEEE Trans. Pattern Anal Mach. Intell., 1984, vol. 6, pp. 721-740. abstract, chapters I, III, IV, IX, XII, Cited in Finnish Search Report.

Hebert et al. A Generalized EM Algorithm for 3-D Bayesian Reconstruction from Poisson Data Using Gibbs Priors IEEE Transactions on Medical Imaging Jun. 1989, vol. 8, No. 2, pp. 194-202 abstract, chapters II and III, Cited in Finnish Search Report.

Nguyen et al. GPU-accelerated 3D Bayesian image reconstruction from Compton scattered data;GPU-accelerated 3D Bayesian image reconstruction from Compton scattered data Physics in Medicine and Biology, Apr. 2011, vol. 56, pp. 2817-2836, I abstract, chapters 1, 2.1, 2.2, 4, Cited in Finnish Search Report.

Zheng et al. Parallelizable Bayesian Tomography Algorithms with Rapid, Guaranteed Congergence IEEE Transactions on Image Processing, Oct. 2000, vol. 9, No. 10, pp. 1745-1759 abstract, chapters I, II, and IV, Cited in Finnish Search Report.

Kayabol et al. Adaptive Langevin Sampler for Separation of t-Distribution Modelled Astrophysical Maps, IEEE Transactions on Image Processing, Sep. 2010, vol. 19, No. 9, pp. 2357-2368 abstract, chapters I, and VII, Cited in Finnish Search Report.

Vintache et al. Iterative Reconstruction for Tramsmission Tomography on GPU Using Nvidia Cuda Tsinghua Science and Technology, Feb. 2010, vol. 15, No. 1, pp. 11-16, ISSN 1007-0214 abstract, introduction, Cited in Finnish Search Report.

Shi et al. A simplified implementation of total variation iterative reconstruction algorithm suitable for parallel computation 2009 IEEE Nuclear Science Symposium and Medical Imaging Conference (NSS/MIC 2009), Orlando, FL, USA, Oct. 24, 2009, pp. 4130-4133, ISBN 978-1-4244-3961-4 ; ISBN 1-4244-3961-2 abstract, chapters I and II, Cited in Finnish Search Report.

Hsieh. Jiang Computed Tomography: Principles. Design, Artifacts, and Recent Advances 2nd ed. Bellingham: SPIE Press, 2009, ISBN 9780470563533 whole document, especially pp. 101-112, Cited in Finnish Search Report.

Finnish Search Report, dated Nov. 28, 2012, from corresponding Finnish application.

* cited by examiner

METHOD, ARRANGEMENT, AND COMPUTER PROGRAM PRODUCT FOR EFFICIENT PRODUCTION OF TOMOGRAPHIC IMAGES

TECHNICAL FIELD

The invention concerns in general the production of tomographic images of an object. Especially the invention concerns a way in which the computational efficiency can be significantly improved when Gibbs sampling is used as a part of generating a Markov chain of sample values.

BACKGROUND OF THE INVENTION

Tomographic imaging as a general concept means producing an image of internal structures of an essentially solid object by observing how certain trans-mitted waves (e.g., acoustic or electromagnetic) or particle beams behave when they pass through such structures. A typical application is medical X-ray tomography, in which the object is a living organism or a part thereof, and the waves used for irradiation are X-rays in the range from a few to some tens of keV or even around a hundred keV. The objective of the imaging process is to make diagnostic observations about such properties of the object that are not readily seen on the surface. Other applications of tomography include, but are not limited to, various industrial processes, in which it is useful to obtain knowledge about what is hidden inside a piece of raw material or a certain product.

For example, log tomography aims at examining logs prior to sawing so that each log could be sawed into planks in the most optimal way.

Figure 1:
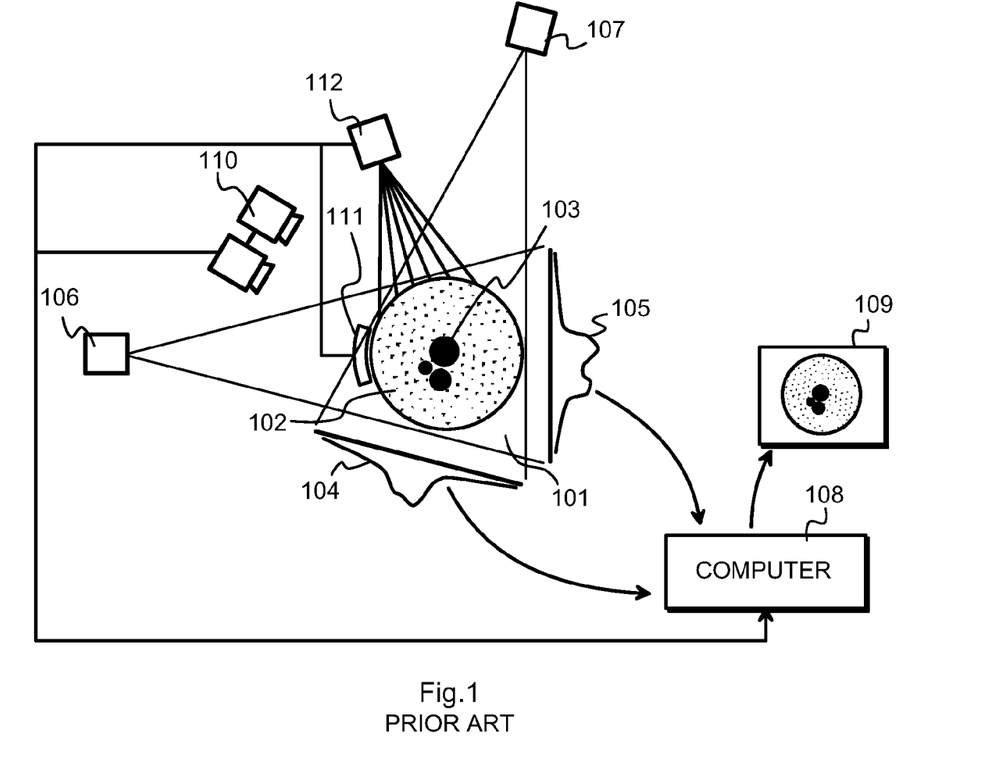
FIG. 1 illustrates the basic principle of computerised tomography.

FIG. 1 illustrates a basic principle of what is known as computerised tomography with sparse angle data in two dimensions. An object 102 is irradiated from a limited number of directions with a radiation source, which in FIG. 1 is shown in two exemplary positions 106 and 107. A spatially sensitive detector, shown correspondingly in two positions 104 and 105, gives spatially bound attenuation information for each exposure. In FIG. 1 the circular regions 103 inside the object 102 are assumed to attenuate radiation more than the bulk of the object. Also, the region 101 outside the object is also assumed to have a different attenuation than the bulk of the object. The readings from the detector and the corresponding irradiation angles are taken into a computer 108, which uses a mathematical reconstruction method to calculate what sort of configuration of attenuation regions is located inside the object 101 in order to give just these particular attenuation profiles. The result of the calculation, which essentially represents an attenuation coefficient map of a two-dimensional slice of the object 102, is shown on a display 109. In order to gather additional information for the measurement, external measurement means like a stereoscopic camera 110, a mechanical measurement arm 111 or a laser scanner 112 can be used to scan the location and form of the outer boundary of the object 102.

An advantageous method for performing tomographic imaging is using statistical inversion, also known as Bayesian statistics. Methods based on this approach are known to produce very good images for limited angle tomography reconstructions. As a mathematical method it is not new, but it has long been regarded as computationally too intensive to be used in practical high resolution tomography applications. However, due to recent advances in algorithms (see, for example, the Finnish patent number FI 116324) and computational capabilities of computers, this method can be seen as a practical alternative.

Bayesian statistics is in essence based on inspecting the posteriori probability density function $$p(x \mid m) = \frac{p(m \mid x)p(x)}{p(m)} \quad (1)$$

that allows us to make inferences about our measurements m together with prior information about the unknown x. In this equation the term $p(m|x)$ is the probability of the measurements, given the model that explains the measurements. This is also known as the likelihood function and it contains the forward model of the tomographic measurement. The density $p(m)$ is the probability of the measurements and it can be viewed as a normalization constant. The term $p(x)$ is the so called prior probability density function. This prior probability density can be used to make prior assumptions about the statistical properties of the unknown x, which is vital for limited angle tomographic reconstruction.

All information of the object is contained within the posterior probability density. However, because this density function is very high-dimensional, it cannot be easily used for visualization. For this purpose, one has to form some sort of estimate. There are two common ways of forming such an estimate: the conditional mean (CM) estimate:

$$\hat{x}_{CM} = \int_0^\infty x \frac{p(m \mid x)p(x)}{p(m)} dx \quad (2)$$

or the maximum a posteriori (MAP) estimate:

$$\hat{x}_{MAP} = \underset{x}{\mathrm{argmax}} \left\{ \frac{p(m|x)p(x)}{p(m)} \right\} \quad (3)$$

The CM estimate $\hat{x}_{CM}$ can be seen as the statistically expected tomographic reconstruction, while the MAP estimate $\hat{x}_{MAP}$ can be seen as the tomographic reconstruction that maximizes the posterior probability density function. In both cases, the nature of the estimators is to find a balance between the likelihood of the measurements $p(m|x)$ and the prior assumptions $p(x)$ of the statistical properties of the unknown x. In Bayesian statistics, the role of the prior distribution is to regularize the solution by adding constraints on the unknown x.

Figure 2:
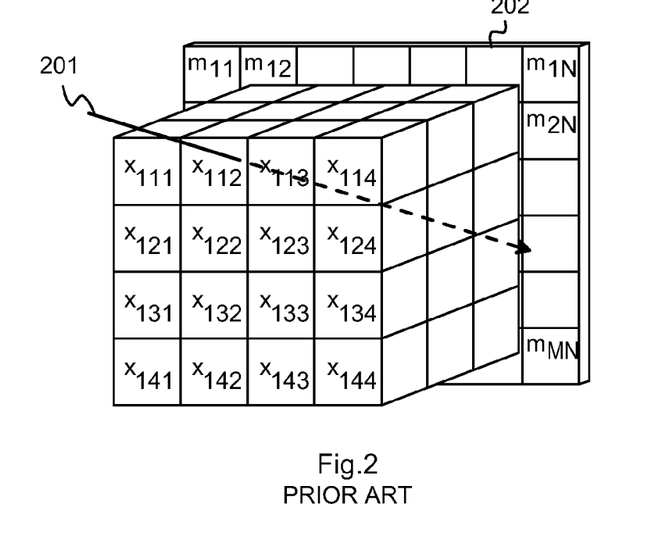
FIG. 2 illustrates a parameterization of a three-dimensional model.
Figure 3:
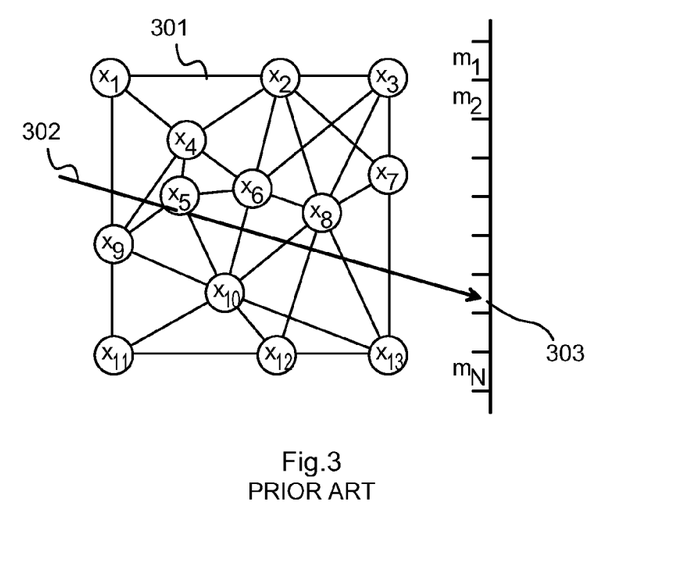
FIG. 3 illustrates a parameterization of a two-dimensional model.

When formulating a forward model for tomography, one needs to parameterize the medium in some way. FIG. 2 shows an exemplary way of doing this, by dividing the modelled region into equally spaced pixels (in the two-dimensional case) or voxels (in the three-dimensional case, illustrated in FIG. 2). FIG. 3 illustrates an alternative parameterization of the medium by using an irregular grid 301. The forward theory of the propagation of the ray along the path of each ray passing from a radiation source to the detector can then be modelled using one of many possible interpolation methods. Examples of rays are shown as 201 in FIGS. 2 and 302 in FIG. 3, and the detector is illustrated schematically as 202 in FIGS. 2 and 303 in FIG. 3. The grid has an exaggeratedly coarse resolution in both FIG. 2 and FIG. 3 for demonstration purposes only. In practice the grid may contain thousands or even millions of points.

Ignoring possible calibration parameters, the likelihood function p(m|x) of a tomographic model is completely defined by the set of model parameters $x_i$, which define the two- or three-dimensional map of attenuation coefficients (or other characteristic descriptors) of the medium. The subscript i refers in general to the way in which the model parameters are identified; for example in FIG. 2 a three-dimensional indexing scheme is utilised (with the parameters of the 16 front voxels illustrated in FIG. 2), and in FIG. 3 a consecutive numbering scheme is utilised. Pixels of the detector are similarly indexed, so that in FIG. 2 we have a two-dimensional detector of M×N pixels and an exemplary two-dimensional indexing scheme $m_{mn}$ of detector pixels, where the indices m∈[1,M] and n∈[1,N]. FIG. 3 illustrates schematically a linear detector of N pixels $m_1, m_2, \ldots m_N$.

So-called Markov chain—Monte Carlo (MCMC) methods can be used for finding the most acceptable value of a random variable x. We may suppose that with respect to a random variable x there is a so-called posteriori distribution. In order to find the most acceptable value of x we generate a Markov chain by starting with some $x_i$ and using a general rule of generating each $x_{i+1}$ from $x_i$ by drawing it from a probability distribution $$D(x_{i+1}|x_i)=p(x_i,x_{i+1}). \quad (4)$$

Supposing now that $$f(y)=\int f(x)p(x,y)dx \quad (5)$$

it follows from ergodic theorems that $$\frac{1}{N}\sum_{i=1}^{N} g(x_i) \to E_f(g(x)) \quad (6)$$

for any measurable function g(x) and the number N of elements in the chain ($x_i$). In other words, we can use the chain ($x_i$) as a simulated sample from the posterior distribution f(x) to calculate e.g. the mean value $E_f(x)$ of x, the posterior variance $E_f(x)^2$ or any higher moments of x.

The two commonly used methods for generating the Markov chain are the so-called Metropolis-Hastings (MH) method and Gibbs sampling. The MH method generates the whole new sample directly whereas Gibbs sampling generates one new component of the vector x at a time. The MH method is relatively fast in all kinds of distributions, but it does not work when the dimension of the random vector x is high. Gibbs sampling works for arbitrarily highly dimensioned vectors x. From the viewpoint of introducing additional constraints, such as a positivity requirement, Gibbs sampling is easy whereas the MH method is not.

A basic principle of all digital image processing is the use of an imaging grid, so that in a two-dimensional case the image consists of a number of picture elements or pixels. A three-dimensional object is modelled in a three-dimensional grid that consists of volumetric pixels known as voxels. Each pixel or voxel is associated with a value, for example in X-ray tomography with an absorption coefficient value, which at the beginning of the calculation is an unknown variable. Together the unknown variables constitute unknown vectors and matrices. The reconstruction process thus involves a large number of matrix calculations, in which the required number of processor operations scale up quadratically or in the third power of the number of image elements. Meaningful results are thus difficult to obtain in reasonable time and with reasonable requirements to computer power. As an example, Gibbs sampling has been considered fast enough for practical applications only in a limited number of distributions.

SUMMARY OF THE INVENTION

It is an objective of the present invention to provide a method, an arrangement, and a computer program product that would improve the computational efficiency of using Gibbs sampling as a part of a MCMC method when applied to computerised tomography.

The objectives of the invention are achieved by recognizing mutually independent points in the reconstruction grid, and by using parallel processing a computer-implemented process to draw the new random values needed in Gibbs sampling in sets, where components in a set are associated with mutually independent points of the reconstruction grid.

A method according to the invention is characterised by the features recited in the independent claim directed to a method.

An arrangement according to the invention is characterised by the features recited in the independent claim directed to an arrangement.

A computer program product according to the invention is characterised by the features recited in the independent claim directed to a computer program product.

Gibbs sampling can be significantly speeded up by utilizing the parallel computing capability offered by multithreading, multicore processing, and/or multiprocessor architectures. However, parallelly drawing the new values from the corresponding conditional distributions is only possible under the condition that the two new values to be drawn parallelly will not affect the calculation of each other in the current or subsequent draws. In other words, the two values must be associated with grid points that are mutually independent.

Two criteria are involved in the mutual independence of grid points. First, the two grid points involved must not belong to each other's immediate surrounding in the grid, where the concept of immediate surrounding is directly linked to the index set used to define the prior distribution. Secondly, there must be no measurement ray that would go simultaneously through both points in the grid. The independence of grid points can be verified by studying the so-called theory matrix. In many cases it can also be perceived intuitively when the measurement geometry and the extent to which neighbouring grid points affect each other in the prior distribution are known.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF EMBODIMENTS OF THE INVENTION

In order to illustrate the theoretical basis of the invention we may briefly recapitulate some basic features of Bayesian statistics and particularly Gibbs sampling.

Concerning terminology, this description uses the concept "tomographic reconstruction" to describe digital data indicative of the values a property of interest at points of an examined object that correspond to the so-called grid points. As was described earlier in association with FIGS. 2 and 3, the reconstruction grid provides a parameterization of the medium through which the measurement rays pass. As a difference to a tomographic image, the tomographic reconstruction itself does not need to have any particular perceived appearance; it may exist simply as a collection of digital data stored in one or more memories. However, once the tomographic reconstruction is known, it is easy to provide different visualizations of it in the form of tomographic images where values read from the tomographic reconstruction are plotted at locations that correspond to the appropriate locations of the grid points within the object.

The prior probability density, also called just the prior for short, restricts the differences between neighbouring model parameters of the tomographic reconstruction. An example of a prior is the following:

$$p(x) \propto ex_p\left(\sum_{i,j \in N'} \frac{|x_i - x_j|^p}{\alpha_{i,j}}\right) \quad (7)$$

where N' is an index set that defines a neighbourhood in the reconstruction grid. In other words, N' is a set of indices (i; j) that correspond to neighbouring model parameters (i; j) of the tomographic model. Neighbouring model parameters are model parameters which are spatially adjacent to each other within the grid, or are otherwise defined to belong to the sphere of influence of each other that must be taken into account. The parameter $\alpha_{i,j}$ determines how strongly we assert smoothness between neighbouring model values $x_i$ and $x_j$. Larger values of $\alpha_{i,j}$ allow larger differences between neighbouring model parameters, and smaller values allow smaller differences, more strongly enforcing smoothness of the model. For irregular grids, the distance between the two points also has to be factored into $\alpha_{i,j}$ in order to consistently enforce smoothness.

Using p=1 for the exponent in the prior density results in total-variation regularization (also known as TV-regularization). Alternatively, the value p=2 would result in the assumption that the differences between the neighbouring model parameters are normally (Gaussian) distributed. The form of regularization that uses p=1 does not penalize sharp transitions as heavily as the Gaussian assumption would.

Another alternative to TV regularization is to assume that the differences are Cauchy distributed, with a probability density function $$p(x) = \prod_{i,j \in N'} \frac{1}{\pi\alpha_{i,j}\left[1 + \left(\frac{x_i - x_j}{\alpha_{i,j}}\right)^2\right]} \quad (8)$$

which has the advantage that the prior density is differentiable everywhere and is scale invariant. Because the distribution has very long tails, it also doesn't unnecessarily discourage sharp transitions in the reconstructed image as Gaussian priors would. In this sense, it can be viewed as an alternative for TV-regularization.

In all of these methods, the parameter $\alpha_{i,j}$ that describes how close to each other the neighbouring values $x_i$ and $x_j$ are assumed to be, can be defined differently for each difference (i;j). If a larger value of $\alpha_{i,j}$ is used, we allow larger differences to occur between $x_i$ and $x_j$. If a smaller value is used, we enforce the neighbouring model parameters $x_i$ and $x_j$ to have values close to each other, i.e., we enforce this region to be more smooth.

There are also other forms of regularization that can be used. For example, it is possible to regularize the value of the model parameters themselves, instead of their differences. Regions in the tomographic reconstruction that are a priori known to have a certain value can be regularized to have that value by assuming that they are inverse Gaussian distributed $$p(x) = \prod_i \left[\frac{\lambda_i}{2\pi x_i^3}\right]^{\frac{1}{2}} ex_p\left(-\frac{\lambda_i(x_i - \mu_i)^2}{2\mu_i^2 x_i}\right) \quad (9)$$

where $\mu_i$ is the expected value of the tomographic reconstruction for the unknown value for parameter $x_i$, and $\lambda_i$ defines the width of the distribution, or how much variation is allowed around the prior assumption. Again, this prior information is highly localized, meaning that we can make different assumptions $\mu_i$ even for each individual one of our model variables $x_i$ if need be. Also other distributions can be used for this purpose.

The most typical form of regularization is only done on the differences of the model parameters $x_i - x_j$. As shown above, it is also possible, if deemed necessary, to regularize the values of the model parameters $x_i$ themselves. These two forms of regularization can also be performed simultaneously by multiplying their corresponding prior probability densities.

In a more generalized sense, one can think of the regularization with the prior density function p(x) as regularization that allows us to enforce various properties on the reconstruction which are localized around a neighbourhood around each of the model parameters $x_i$. The prior information used to regularize the problem doesn't necessarily have to be restricted to the above examples. The neighbourhood can be a larger region of parameters around $x_i$ if necessary. According to an aspect brought forward in the U.S. patent application Ser. No. 13/285,140 of the same assignee, which is incorporated herein by reference, prior information can be defined in a localized manner and different localized regions of the model x can be assigned different prior information.

Let us consider Gibbs sampling, relying on our assumption about a posterior distribution f(x) but this time with an N-dimensional vector-valued random variable x, the components of which are $(x_1, x_2, x_3, \ldots, x_N)$. Gibbs sampling involves generating a next version of said vector-valued random variable by drawing for each component a value from a conditional distribution. Repeatedly doing the same creates a Markov chain. In a formally appropriate notation we designate the transformation step needed in the generation of a Markov chain as changing x into another vector $v=(v_1, v_2, v_3, \ldots, v_N)$ in the following way:

Draw $v_1$ from the distribution $f(x_1|x_i, i\neq 1)$:

$$D(y_1) - f(y_1, x_2, x_3, \ldots x_N) \quad (10)$$

then draw $y_2$ so that $$D(y_2) - f(y_1, y_2, x_3, \ldots, x_N) \quad (11)$$

and continue until $$D(y_N) - f(y_1, y_2, y_3, \ldots, y_N) \quad (12)$$

This procedure defines a random transformation x→y. We may denote the probability density of the transformation as p(x,y)=D(y|x) and it is easy to see that this conforms with the pattern discussed earlier in the description of background (see equation 4). Gibbs sampling involves essentially generating random numbers from one-dimensional distributions. For certain special distributions, like uniform, normal (Gaussian), exponential, and some others, that is easy to implement. In the general case, however, we must use the independently known fact that the function $F^{-1}(r)$ has the density of f, if r is a uniformly distributed random number and F is the distribution function of f. Performing Gibbs sampling with a general posteriori distribution f involves calculating F, i.e. integrating the function f over a range that is wide enough to ensure that outside it the probability density is essentially zero. Numerical integration of this kind can be extremely time-consuming even with best computers and algorithms, if the problem is large.

If we have got the posterior density f by inverting the linear direct theory $$m=Ax+\epsilon \quad (13)$$

where m represents detection results, A is the theory matrix, x is a vector of unknown variables and $\epsilon$ is an error term, the density D(x) is $$D(x) \approx ex_p\left(-\frac{1}{2}(m-Ax)^T \sum{}^{-1} (m-Ax)\right) \quad (14)$$
$$\approx ex_p\left(-\frac{1}{2}x^T Q x - 2x^T v + C\right)$$

where $Q=A^T\Sigma^{-1}A$, $v=A^T\Sigma^{-1}m$, $\Sigma$ is the error covariance matrix (which is diagonal if we assume that measurements are independent of each other in this sense) and C does not depend on x. We can thus calculate the centerpoints of one-dimensional conditional distributions without calculating the centerpoint of the whole posteriori density. Calculating the last-mentioned would be time-consuming if the number of unknowns is large.

A Gaussian (non-proper) prior $D_{pr}(x)$ is of the form $$D_{pr}(x) \approx ex_p\left(-\sum_{i,j\in N'} \frac{(x_i - x_j)^2}{d_{ij}^2}\right) \quad (15)$$

where N' is the set of such indices (i; j) that $x_i$ and $x_j$ are neighboring points, and $d_{i,j}$ is the regularization error, which here has the role of a standard deviation and controls the relation between the measurement and a priori information in the calculation of the reconstruction. Giving indices to the regularization error only comes into question if it is allowed to change between grid points; some formulae like equation (15) treat the regularization error as a constant parameter. The fact that the prior is "nonproper" means that an integral of the prior itself would have an infinite value. A total variation (TV-) prior is of the form $$D_{pr}(x) \approx ex_p\left(-\sum_{i,j\in N'} \frac{|x_i - x_j|}{d_{ij}}\right) \quad (16)$$

and may have a positive real number s as an exponent to the absolute difference value, i.e. $|x_i-x_j|^s$ in the term to be summed instead of just $|x_i-x_j|$.

According to an aspect of the present invention, it is possible to calculate $y_i$ and $y_j$ in parallel to significantly speed up the Gibbs sampling, when certain rules are obeyed. We may recall that calculating $y_i$ (or $y_j$) is synonymous to drawing, for the i:th (or j:th) component of the vector-valued variable, a value from a conditional distribution. The draw $D(y_i)$ can be calculated in parallel with the draw $D(y_j)$ when:

(rule 1): i≠j and
(rule 2): $y_i$ does not affect the calculation of $y_j$ in current or subsequent draws.

Another way to express the content of these rules is to say that the components $y_i$ and $y_j$ represent unknowns associated with mutually independent points of the reconstruction grid. The requirement of mutual independence in turn has two important implications. Firstly, concerning prior distributions, the indices i and j cannot both belong to the same index set $N^i$ (see equations (7) and (8)). Secondly, from the measurement geometry comes the requirement that the coefficient of $x_ix_j$ in $x^TQx$ (in formula 14) must be zero; that is, $2Q_{i,j}=0$. This is true when there exists no such measurement k that the elements $a_{ki}$ and $a_{kj}$ in the theory matrix A (see formulae 13 and 14) would be non-zero simultaneously. Thinking about the measurement geometry, this last-mentioned implication is understood as meaning that no linearly propagating measurement ray is allowed to pass through both the i:th and the j:th point in the reconstruction grid on its way from the radiation source to the detector.

Figure 4:
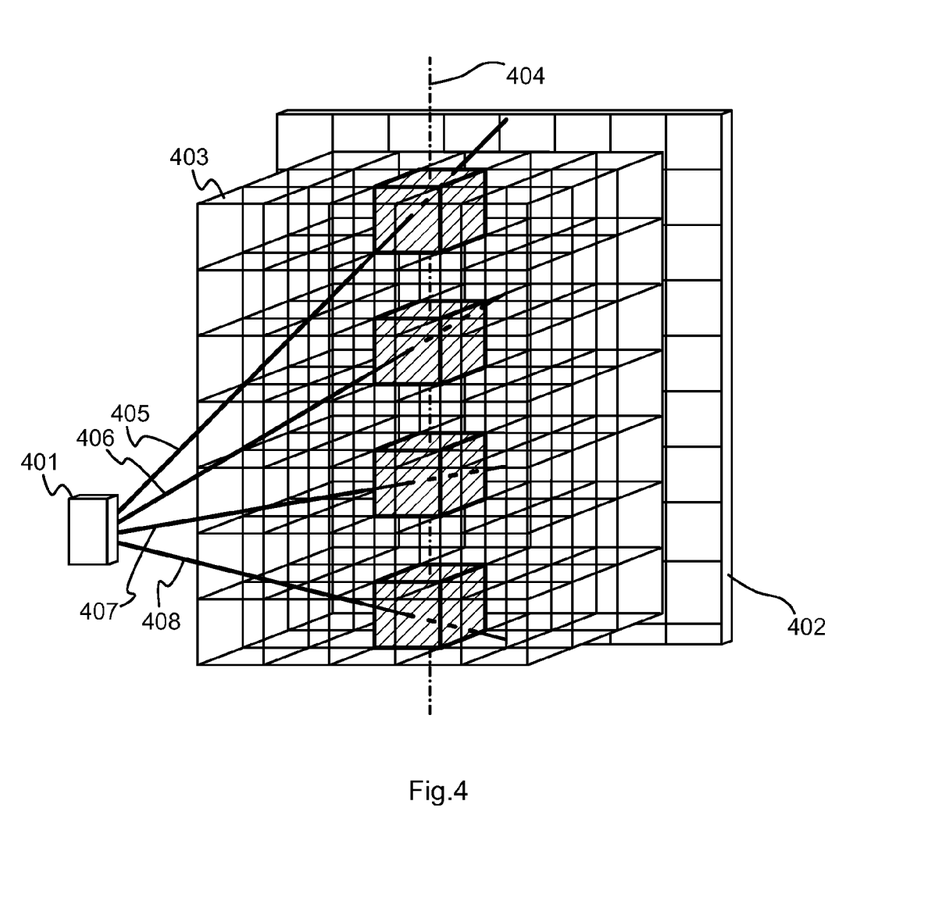
FIG. 4 illustrates mutually independent grid points in an exemplary case.

FIG. 4 illustrates a simplified example of selecting certain points of the reconstruction grid that are mutually independent in the sense explained above. Measurement rays are generated at a radiation source 401 and each of them propagates linearly to a detector 402. On their way they pass through a medium that has been parameterized with the help of a reconstruction grid 403. The grid has been illustrated as exaggeratedly coarse to enhance graphical clarity; it consists of a 3×5 array of vertical columns, each comprising seven (7) grid points. In order to get different exposures with multiple views of the examined object, a mechanical arrangement (not separately shown) is configured to rotate the radiation source 401 and the detector 402 facing each other around a vertically oriented rotational axis 404 that here passes through the centremost column of the reconstruction grid.

Non-adjacent grid points that are in the same vertical column will never be hit by the same measurement ray in the geometry of FIG. 4. Examples of four different measurement rays 405, 406, 407, and 408 are shown. We may assume that the definition of the index set $N^i$ is such that it only includes the immediately adjacent grid points. If that is the case, in any linear direction through the reconstruction grid 403 taking every second grid point results in a set of grid points that are not in the neighbourhood of each other. Thus for example the four hatched grid points in FIG. 4, i.e. the $1^{st}$, $3^{rd}$, $5^{th}$, and $7^{th}$ grid point of the centremost column, satisfy the criteria of being mutually independent points of the reconstruction grid. In a common rotational circle geometry one can easily divide each vertical column into sets of mutually independent points based on chosen interpolation (which is used in creating the theory matrix A) and the prior neighbourhood size. For example, with nearest neighbourhood interpolation and TV or corresponding Gaussian prior, each vertical column in three-dimensional space can be divided into two sets, each including mutually independent points, by taking to the first set every second point in the column and to the second set the remaining points of the column.

In some widely applied geometries, tomographic reconstruction is performed from different exposures with multiple views of an examined object, which different exposures have been obtained by rotating a radiation source and a detector facing each other around said object about a vertically oriented rotational axis. In such cases in general, mutually independent points of the reconstruction grid can be obtained by selecting, from at least one vertical column of the reconstruction grid, every n:th point, where n is an integer larger than or equal to two.

Figure 5:
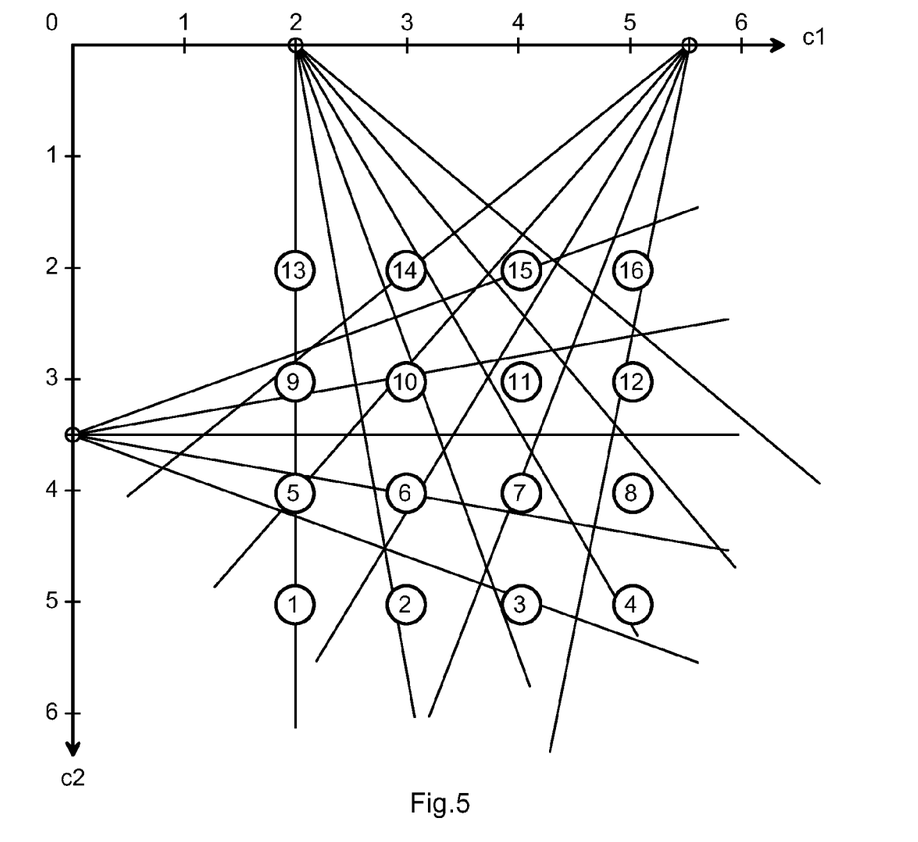
FIG. 5 illustrates a simple two-dimensional grid.

FIG. 5 illustrates another simplified example, in which the reconstruction grid is two-dimensional and consists of sixteen (16) points located in a regular rectangular configuration at one step from each other between $c1\epsilon[2, 5]$ and $c2\epsilon[2, 5]$. From the measurement geometry it is known that three exposures will be taken, with the radiation source at points (2, 0), (5.5, 0), and (0, 3.5) respectively. The attenuation coefficients or other interesting unknowns that are associated with the points 1, 2, 3, . . . , 16 of the reconstruction grid could be represented with the components $x_1$, $x_2$, $x_3$, . . . , $x_{16}$ of a vector-valued variable x. For the purposes of the invention, said components of the vector-valued variable should be divided into sets, so that components in a set represent unknowns associated with mutually independent points of said reconstruction grid.

We assume that the concept of a neighbourhood in the reconstruction grid is defined as only including directly (horizontally and vertically) adjacent grid points, and not including diagonally adjacent ones. Remembering that points of the reconstruction grid are mutually independent if 1) they are not in each other's neighbourhood and 2) no measurement ray will pass through both of them, for example the following division into sets can be made:

{$x_1$, $x_4$, $x_7$} (associated with grid points 1, 4, and 7)
{$x_3$, $x_9$, $x_{11}$} (associated with grid points 3, 9, and 11)
{$x_2$, $x_8$, $x_{15}$, $x_{16}$} (associated with grid points 2, 8, 10, and 16)
{$x_5$, $x_{12}$, $x_{14}$} (associated with grid points 5, 12, and 14)
{$x_6$, $x_{13}$$x_{15}$} (associated with grid points 6, 13, and 15)

In a general case with arbitrary measurement geometry, the sets of mutually independent points can be identified by studying the theory matrix A and identifying the points for which the previously mentioned condition (no simultaneously non-zero values of elements $a_{ki}$ and $a_{kj}$) is true.

In this description a set means a finite collection of objects in which order has no significance, and multiplicity is generally also ignored.

Figure 6:
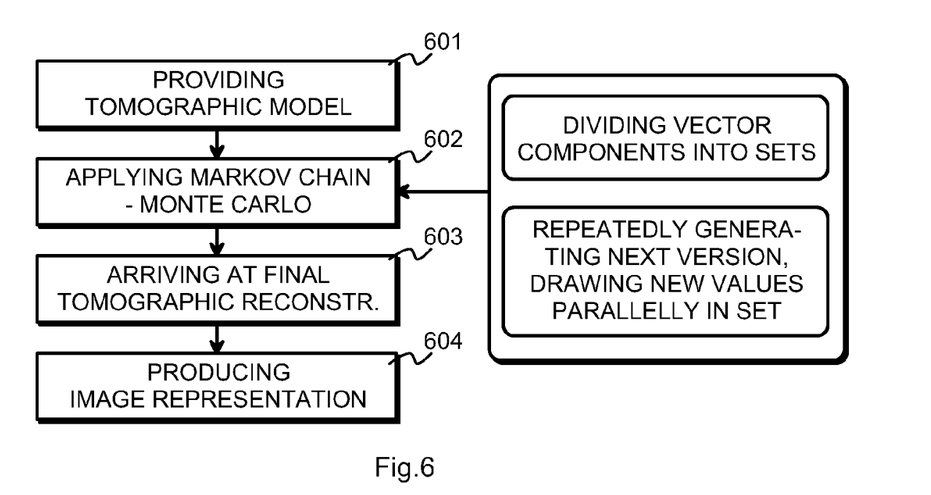
FIG. 6 illustrates a method according to an embodiment of the invention.

FIG. 6 illustrates schematically a method according to an embodiment of the invention. Step 601 comprises providing a tomographic model, which includes representing unknowns that are associated with points of a reconstruction grid with components of a vector-valued variable. Applying a Markov chain—Monte Carlo method at step 602 comprises repeatedly generating a next version of said vector-valued variable by drawing for each component a value from a conditional distribution. As is illustrated in more detail on the right, step 602 comprises dividing components of the vector-valued variable into sets, so that components in a set represent unknowns associated with mutually independent points of the reconstruction grid. For at least two components of a set, the drawing of values from a conditional distribution can be performed in parallel in a computer-implemented process. This parallelism makes the calculation much more efficient than in prior art methods.

The division of the components $x_i$ of a vector-valued variable x into N separate sets can be written as follows:

$$\{x_{i1_1}, x_{i2_1}, \ldots, x_{i_{m_1}1}\} \quad (17)$$
$$\{x_{i1_2}, x_{i2_2}, \ldots, x_{i_{m_2}2}\}$$
$$\vdots$$
$$\{x_{i1_N}, x_{i2_N}, \ldots, x_{i_{m_N}N}\}$$

In this expression each pair of curly brackets encloses the components belonging to one set. The index i represents the identifier of the respective component in the composition of the original vector-valued variable x. The first subindex, which ranges from 1 to $m_1$, $m_2$, or $m_N$, denotes the ordinal number of the component within the set; it should be noted that different sets may have different number of components, and in general the k:th set includes $m_k$ components, where $k\epsilon[1N]$. The second subindex, which is 1 for all components in the first set, 2 for all components in the second set, and N for all components in the N:th set, just identifies the component as belonging to that particular set.

Parallel drawing of new values can be accomplished within a set. Let us first examine the first set, i.e. the topmost line in expression (15). Generating a next version involves drawing $y_{i_{11}}$ from the distribution $f(x_{i_{11}}|x_i, i \neq i_{11})$:

$$D(y_{i_{21}}) \sim f(y_{i_{11}}, x_{i_{21}}, x_{i_{31}}, \ldots x_{i_{m1}}, x_{i_{12}}, \ldots) \quad (18)$$

and drawing simultaneously also $y_{i_{21}}$, $y_{i_{21}}$, . . . $y_{i_{m11}}$ from the respective distributions $$D(y_{i_{21}}) \sim f(x_{i_{11}}, y_{i_{21}}, x_{i_{31}}, \ldots, x_{i_{m_{11}}}, x_{i_{12}}, \ldots) \quad (19)$$
$$D(y_{i_{31}}) \sim f(x_{i_{11}}, y_{i_{21}}, x_{i_{31}}, \ldots, x_{i_{m_{11}}}, x_{i_{12}}, \ldots)$$
$$\vdots$$
$$D(y_{i_{11}}) \sim f(x_{i_{11}}, y_{i_{21}}, x_{i_{31}}, \ldots, x_{i_{m_{11}}}, x_{i_{12}}, \ldots)$$

Bold typeface has been used solely to make it easier for the reader to perceive, which one is the new value on each line.

Note that here the distributions do not actually depend on the values in the first set, due to the mutual independence of the corresponding grid points.

After the new component values $y_{i_{11}}, y_{i_{21}}, y_{i_{31}}, \ldots y_{i_{m11}}$ for the first set have been drawn, we may proceed to drawing new values for the components in the second set. This can again be accomplished in parallel (with the new value emphasized here in bold):

$$D(y_{i_{12}}) \sim \quad (20)$$
$$f(y_{i_{11}}, y_{i_{21}}, \ldots, y_{i_{m11}}, \mathbf{y_{i_{12}}}, x_{i_{22}}, \ldots, x_{i_{m22}}, x_{i_{13}}, \ldots)$$

$$D(y_{i_{22}}) \sim$$
$$f(y_{i_{11}}, y_{i_{21}}, \ldots, y_{i_{m11}}, y_{i_{12}}, \mathbf{x_{i_{22}}}, \ldots, x_{i_{m22}}, x_{i_{13}}, \ldots)$$
$$\vdots$$
$$D(y_{i_{m22}}) \sim f(y_{i_{11}}, y_{i_{21}}, \ldots, y_{i_{m11}}, y_{i_{12}}, x_{i_{22}}, \ldots, \mathbf{x_{i_{m22}}}, x_{i_{13}}, \ldots)$$

Note that this explanation proceeds in strict order with the first, second, etc. set, but actually the sets can be handled in arbitrary order (which is synonymous to saying that the naming of the sets into first, second, etc. can be done arbitrarily). Doing the same for all sets eventually produces the complete next version of the whole vector-valued variable. The generation of the next version was previously referred to as the transformation $x \rightarrow y$.

One possibility of implementing the parallel drawing of values from the respective conditional distributions is to do it in parallel threads of a computer-implemented process. In general, a thread is known as the smallest unit of processing that can be scheduled by an operating system. In the hierarchy of concepts, a thread is typically conceived as contained inside a process. Multiple threads may exist within a common process and they may (but need not) share common resources such as memory, file handles, and others. The threads of a process as seen as sharing the code (i.e. machine-readable instructions) of the process as well as the context of the process, which as a concept refers in particular to the values that variables of the process refer to at a given moment.

Figure 7:
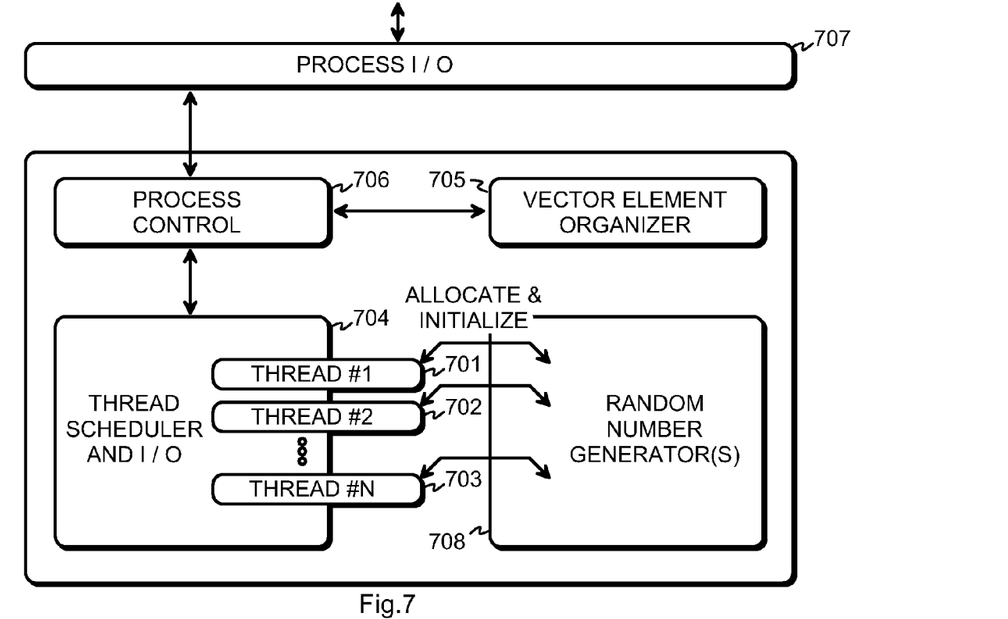
FIG. 7 illustrates the use of parallel threads.

FIG. 7 illustrates conceptually the implementation of a number of parallel threads 701, 702, and 703, each of which comprises machine-readable instructions that, when executed by a processor, cause the implementation of drawing a value from the appropriate conditional distribution. The execution of the threads can be made parallel and is scheduled by a thread scheduler and input/output unit 704. Another unit 705 is shown for dividing the components of a vector-valued variable into sets and for maintaining the organization of the vector elements while the draws proceed. A process control unit 706 is schematically shown, which is responsible for the overall execution of the process, and exchange of information with other processes is shown to take place through a process input/output unit 707.

Each time when a value is drawn from a conditional distribution, at least one random value is needed. To be quite exact, computers can only produce pseudorandom numbers, but since a properly initialized and used computer-implemented random number generator provides a reasonably good simulation of true randomness, it is conventional to refer to its output as random numbers. In the case of parallelly drawing values from conditional distributions in different threads, care must be taken to ensure that randomness is not sacrificed. If, for example, an exactly similar random number generator would be used in all threads with a common seed, certain non-randomness could be invoked. A good way to ensure proper randomness in each of said parallel threads is to have each thread allocate and initialize a random number generator independently of other threads for the drawing of a value from the corresponding conditional distribution. The random number generators are schematically illustrated in FIG. 7 as the unit 708.

In addition and/or as an alternative to the use of parallel threads, parallel computing can also be implemented in parallel cores of a multicore processor, and/or in parallel processors of a multiprocessor architecture. In this sense, parallel cores may mean actual, physical cores of a multicore processor, or virtual cores. The use of virtual cores is sometimes referred to as hyperthreading. Comparing to the multithreading example shown in FIG. 7, the thread scheduler and input/output unit 704 could be augmented and/or replaced with a more versatile scheduler and input/output unit that is capable of distributing data, scheduling the processing, and coordinating results between whatever kinds of parallel computing entities are available. Also with parallel cores or parallel processors, the process should comprise allocating and initializing a random number generator independently of other cores or processors for the drawing of a value from the corresponding conditional distribution, in order to maintain the appropriate randomness. In principle it would be possible to make several threads, cores, processors or other parallel processing units share a common, sequentially addressed random number generator, but that could have disadvantageous consequences to processing efficiency, because calls to the random number generator would need to check the momentary availability of the random number generator and/or to include a queuing routine.

Referring back to FIG. 6, step 603 comprises completing the calculation by arriving at a final, acceptable form of the tomographic reconstruction. Devising and implementing criteria that define when the MCMC method is allowed to stop is known as such from the technology of computerized tomography, and the present invention does not place any particular limits to how these criteria should be applied. Step 604 comprises using the completed tomographic reconstructions to produce an image representation for example on a display. Also this step can be similar to the corresponding steps known from previous computerized tomography solutions.

Figure 8:
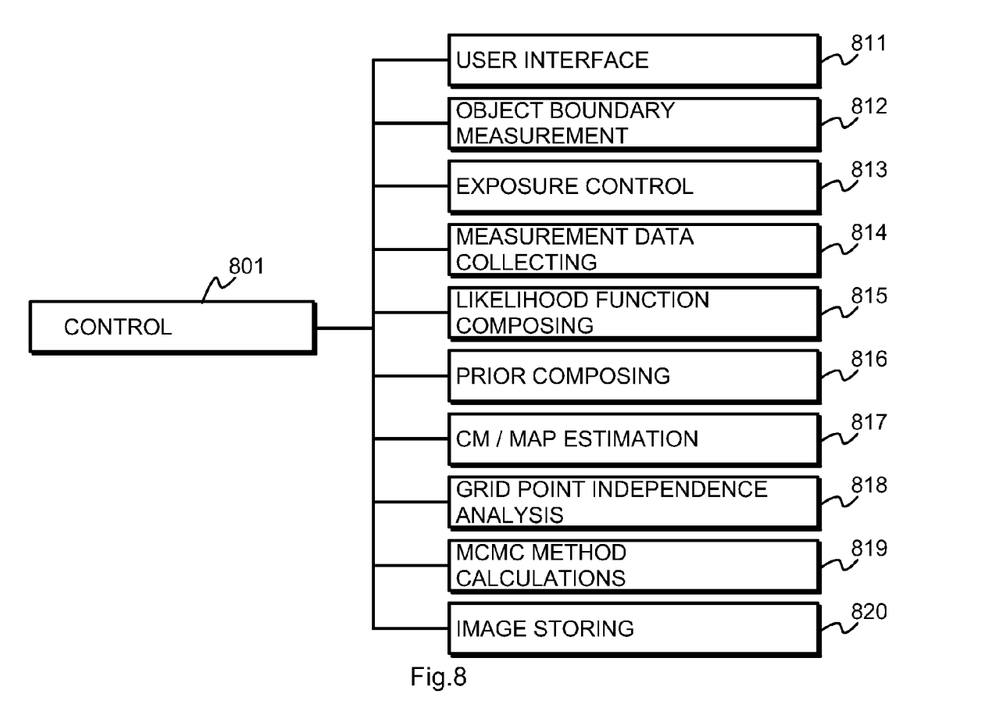
FIG. 8 illustrates a computer program product according to an embodiment of the invention.

FIG. 8 is a schematic illustration of an exemplary computer program product according to an embodiment of the invention. The overall control of executing computerized tomography is contained in a control section 801, which has bidirectional communications with all other sections of the machine-readable instructions. A user interface section 811 is responsible for exchanging information with a human user, for example displaying images graphically and receiving user input. An object boundary measurement section 812 comprises the machine-readable instructions that concern the task of making auxiliary measurements about the object. An exposure control section 813 comprises the machine-readable instructions that control the illumination of the object to be examined with X-rays. A measurement data collection section 814 comprises the machine-readable instructions that control the acquisition of measurement data from the X-ray detectors and/or possible other sources of measurement data. A likelihood function composing section 815 comprises the machine-readable instructions that control the forming of the forward model of the tomographic measurement and the term $p(m|x)$, i.e. the probability of the measurements, given the model that explains the measurements.

A prior-composing section 816 comprises the machine-readable instructions that control the forming of the prior probability density function, which is also known as the prior for short. A CM and/or MAP estimation section 817 comprises the machine-readable instructions that control the calculation of the so-called CM (conditional mean) and/or the so-called MAP or maximum a posterior estimate. Section 818 comprises the machine-readable instructions that control the analysis of grid points (i.e. the theory matrix) for mutual independence, in order to be able to recognize mutually independent points and to compose the sets for parallel drawing of values from conditional distributions.

A MCMC method calculations section 819 comprises the machine-readable instructions that control the execution of the MCMC method, i.e. representing unknowns that are associated with points of a reconstruction grid with components of a vector-valued variable, and repeatedly generating a next version of said vector-valued variable by drawing for each component a value from a conditional distribution. As was described above, said components of the vector-valued variable are divided into sets, wherein components in a set represent unknowns associated with mutually independent points of said reconstruction grid. For at least two components of a set, said drawing of values from a conditional distribution is performed in parallel in a computer-implemented process.

An image storing section 820 comprises the machine-readable instructions that control the storing of image representations.

Figure 9:
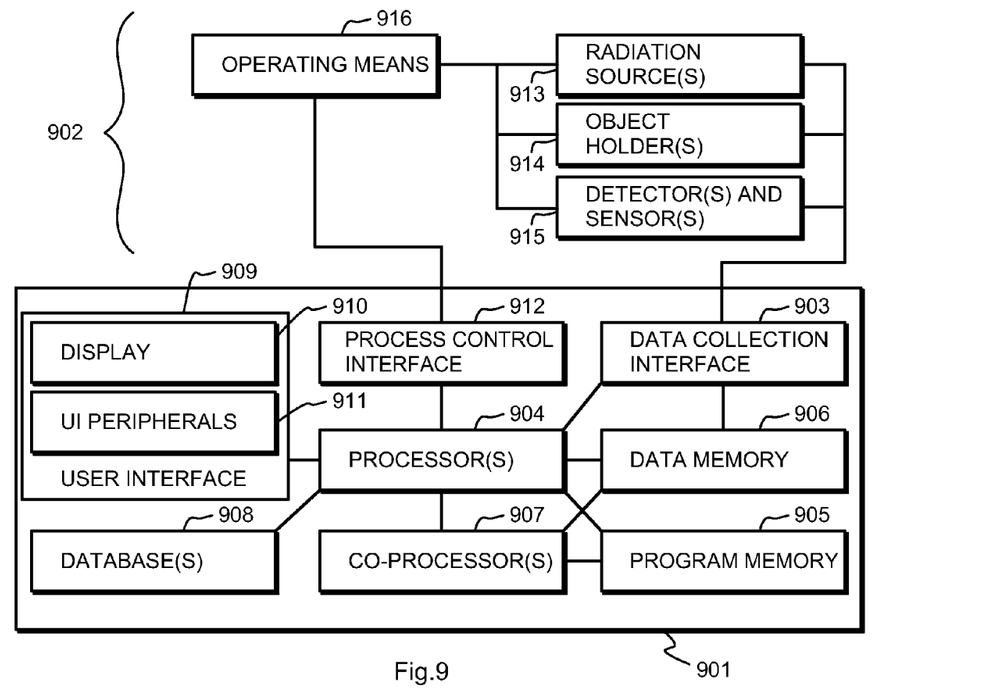
FIG. 9 illustrates an arrangement according to an embodiment of the invention.

FIG. 9 is a schematic representation of an apparatus according to an embodiment of the invention. Major parts of the apparatus of FIG. 9 are a computer section 901 and an X-ray imaging section 902. The former comprises a data collection interface 903 configured to obtain a set of measurement data representative of attenuation experienced by electromagnetic waves that propagated through parts of an object to be examined. In the apparatus of FIG. 9 this is illustrated as a direct communications connection from the X-ray imaging section 902, but it should be noted that a tomographic reconstruction according to embodiments of the invention can be created also in standalone computer devices, which do not have an X-ray imaging section of their own but receive measurement data that has been previously produced elsewhere.

The computer section 901 comprises a processor 904 that is configured to represent the object to be examined with a tomographic model that comprises grid points that represent parts of the object to be examined and to apply statistical inversion to convert said set of measurement data into a calculated distribution of attenuation values associated with at least a number of said grid points. The program that the processor executes is stored in a program memory 905. There may be a separate data memory 906 for storing data, and there may be co-processors 907 (such as arithmetical processors) that take part in making the calculations. Especially there may be a number of processors configured for parallel multithread computing. The processor 904 may also have one or more databases 908 at its disposal for storing and retrieving large amounts of data and for storing function libraries and other kinds of resources.

The processor 904 is configured to represent unknowns that are associated with points of the reconstruction grid with components of a vector-valued variable, to repeatedly generate a next version of said vector-valued variable by drawing for each component a value from a conditional distribution, and to use the components of a so generated version of said vector-valued variable as a tomographic reconstruction. The processor 904 is also configured to divide components of the vector-valued variable into sets, wherein components in a set represent unknowns associated with mutually independent points of said reconstruction grid, and to perform, for at least two components of a set, said drawing of values from a conditional distribution in parallel in a computer-implemented process.

For producing graphical images of tomographic reconstructions, the computer section 901 of FIG. 9 comprises a user interface 909, which in FIG. 9 is shown to comprise at least a display 910 and some user interface peripherals 911. Such peripherals may be used for example to convey user input from a human user to the processor.

A process control interface 912 links the computer section 901 with the X-ray imaging section 902, which is configured to controllably irradiate the object to be examined with X-rays and to detect intensities of X-rays that passed through parts of the object to be examined in order to produce the previously mentioned set of measurement data. Parts of the X-ray imaging section 902 that are shown in FIG. 9 are the radiation source(s) 903, the object holder(s) 914, and one or more detector or sensor 915. Operating means 916 are shown as the control entity that operates the radiation source(s) 903, the object holder(s) 914, and the detectors and/or sensors 915 according to the commands it receives from the computer section 901.

In the description given so far, the use of parallel processing has been explained to mean parallelly drawing values from a conditional distribution for at least two components of a set. As has been explained, the components in a set represent unknowns associated with mutually independent points of the reconstruction grid. However, as an important generalisation of the parallel processing concept, in some cases also different sets or combinations of sets can be processed in parallel with each other. This necessitates defining the additional concept "independent collections". Two groups of grid points are mutually independent, and form the basis for two mutually independent collections, if every grid point of the first group is mutually independent with every grid point in the second group. It should be noted that grid points of a group need not all be independent of each other; a collection may comprise several sets, so that only within each individual set the requirement of mutual independence is fulfilled.

An intuitive way of perceiving independent collections is associated with regular, rectangular, three-dimensional grids, where independent collections can be associated with suitably selected vertical columns of the grid. For this reason, also the designation "independent columns" can be used. Let us assume a regular, rectangular, three-dimensional grid and an imaging geometry where the radiation source and the detector rotate around the grid in a horizontal plane (see FIG. 4, for example). Previously we have shown that within an individual column, a division into sets can be made by selecting every second, every third, or in general every n:th (where n is a positive integer larger than or equal to two) point in that column, depending on how the concept of neighbourhood has been defined.

Two columns are independent of each other, and thus form the basis for two mutually independent collections, if all components in the sets formed in the first column represent unknowns associated with points of the reconstruction grid that are independent of all points, the unknowns associated with which are represented by components of sets formed in the second column. In short, the points of the first column must not be in the neighbourhood of the points in the second column, and no measurement ray must pass through both the first and second columns.

Figure 10:
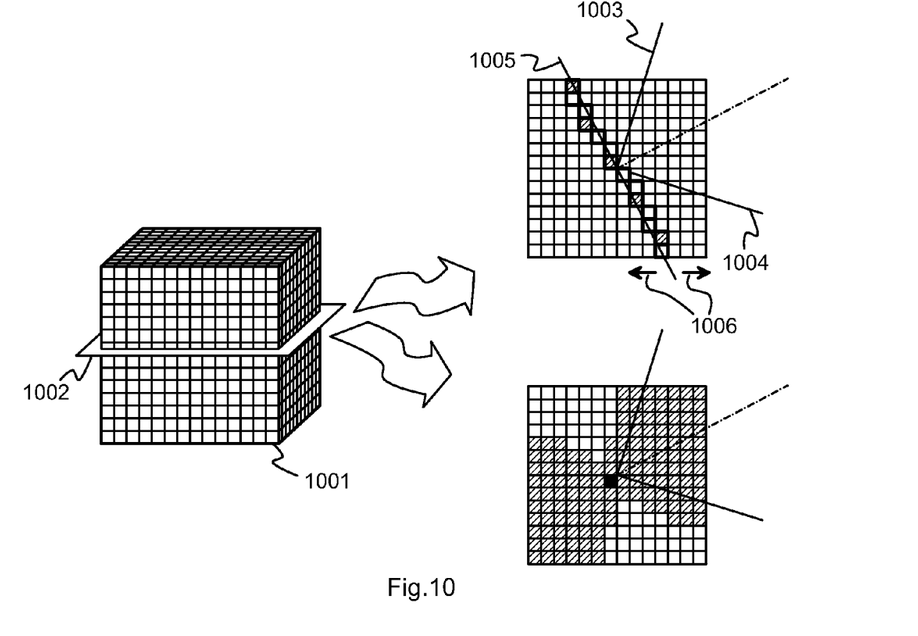
FIG. 10 illustrates aspects of selecting independent columns.

In the geometry described above, the selection of independent columns can be made by taking a horizontal cross section of the grid (which is a two-dimensional rectangular grid) and identifying points that in that cross-section are independent of each other. FIG. 10 illustrates two examples of methods for selecting mutually independent columns. A horizontal cross section is taken along plane 1001 of the regular rectangular grid 1002. At the top right, there is illustrated a method for selecting mutually independent columns that is applicable especially if the measurement will be made within a limited angle, which is significantly smaller than 180 degrees. Here we assume that the tomographic measurement will involve imaging the object from a 90 degrees angle. In other words, the radiating directions will range from the direction illustrated with line 1003 to the direction illustrated with line 1004, which is at a 90 degrees angle with line 1003.

The method comprises taking a central line (illustrated in FIG. 10 as the dashdot line) that divides the range of radiating directions in half, and drawing a line 1005 that is perpendicular to said central line across the cross section of the grid. This last-mentioned line is pixelized at the resolution of the cross section of the grid; in other words, those grid points are marked that form a jagged path following the last-mentioned line across the cross section of the grid. From these grid points, every second, every third, or in general every n:th (where n is a positive integer larger than or equal to two) grid point is selected so that none of the measurement rays, not even the most extreme ones along lines 1003 and 1004, will go through two of the selected grid points. The minimum value of n depends on the angle between lines 1003 and 1004, as well as on the resolution of the grid. The columns that in the complete grid correspond to the selected grid points are mutually independent. In the example of FIG. 10, n=3 and the hatched grid points illustrate mutually independent columns.

From the marked grid points, n groups of mutually independent columns can be identified. When these have been dealt with, each following n groups of mutually independent columns can be identified by shifting the jagged path of marked grid points in a selected direction across the cross section. The arrows 1006 illustrate such shifting.

The lower right part of FIG. 10 illustrates another exemplary method for selecting mutually independent columns. For the sake of simplicity, we assume the same measurement geometry as above, although it should be noted that both the invention in general and the exemplary methods for selecting independent columns in particular are applicable to tomographic measurements with narrow ranges of viewing angles; tomographic measurements with sparse measurement angles; and tomographic measurements with imaging from irregularly spaced directions.

First, a grid point is selected at or close to the centre of the cross section. The selected grid point is shown black in FIG. 10. Then all those other grid points are marked that will be along a same measurement ray as the selected grid point at some of the radiating directions. The marked grid points are shown hatched. Among the grid points that remain unmarked, a next grid point is selected either at random or at least partly following a particular selection strategy. For example, a selection strategy might call for always selecting the unmarked grid point that is closest to (or farthest from) an already selected grid point, or randomly selecting among those grid points that form the current borderline of the area of unmarked grid points. When the selection of said next grid point has been made, the "shadowed" grid points (i.e. those that will be along a same measurement ray with the last selected grid point at some of the radiating directions) are again marked. The same process (selecting a next unmarked grid point and marking those shadowed by it) is repeated until no more unmarked grid points are left. The selected grid points indicate mutually independent columns in the grid.

When independent columns have been identified, the maximum number of parallel processing units that can be employed is the number of independent columns times the number of independent points in a set that has been defined within a column. However, it is not always advisable to pursue the maximum amount of parallelisation in the processing. The potential for speeding up the actual drawing of new values by parallelisation must be balanced with respect to the possible delays caused by frequent synchronization. Synchronization means that the most recently (parallelly) drawn new values are communicated to those parts of the arrangement that need to take them into account on the next round of drawing values for the components that again are associated with mutually independent points.

The concept of independent collections can be utilised to that each independent collection is allocated to one thread, core, processor, computer, or other calculating unit capable of operating in parallel with other similar calculating units. This way it is ensured that synchronization between parallel calculating units needs to be performed only after the new values for all components in the collection have been drawn. The advantage comes from the fact that synchronization between calculating units may have to be performed over a communications medium that is inherently slow compared to the rate at which operations can be performed inside an individual calculating unit.

In some cases even a two-tier hierarchy of parallel computing can be used. For example, we may assume that there are a number of processors capable of operating in parallel, and within each processor there are a number of cores or threads capable of operating in parallel with each other. If an independent collection is allocated to a processor, and sets of the above-described kind exist within that collection, the processor may further allocate the drawing of new values for each component in a set to the parallel cores or threads. After taking care of a first set, synchronization needs to be performed between the cores or threads of that processor before they can commence drawing new values for the components of a second set, but it is probable that synchronization within a processor is faster than synchronization between processors. The latter only needs to be performed after the new values for all components in the independent collection have been drawn.

The choice regarding how the parallel processing is organized (parallelly drawing values for the components of a set; parallelly drawing values for independent collections; or even two-tier hierarchy of parallel computing where independent collections are processed in parallel and within a collection the components that constitute a set are processed in parallel) is advantageously made by taking into account the dimensions of the problem, the possibility of identifying independent collections, the number of components in a set, as well as the number, availability, and mutual communications efficiency of parallel processing units. Typically if the measurement angle is limited and/or there are only few measurement directions, it is most advantageous to primarily rely on independent collections. On the other hand, for example in large medical imaging problems where the number of projections is large and/or the imaging angle is at least 180 degrees, there may be so few independent collections that it is better to organize the parallel processing based on the independent components in a set.

A major advantage of embodiments of the present invention is the significantly improved efficiency of performing Gibbs sampling as a part of providing a tomographic reconstruction, because parallel computing can be applied to drawing the new values for the vector-valued variable from the appropriate conditional distributions. The exemplary embodiments of the invention that have been described above should not be construed to place limitations to the scope of protection that is defined by the appended claims.

We claim:

1. A method for constructing a tomographic reconstruction through the application of statistical inversion, comprising:
representing unknowns that are associated with points of a reconstruction grid with components of a vector-valued variable,
repeatedly generating a next version of said vector-valued variable by drawing for each component a value from a conditional distribution, and
using the components of a so generated version of said vector-valued variable as said tomographic reconstruction;
wherein:
said components of the vector-valued variable are divided into sets, wherein components in a set represent unknowns associated with mutually independent points of said reconstruction grid, and
for at least two components of a set, said drawing of values from a conditional distribution is performed in parallel in a computer-implemented process.

2. A method for constructing a tomographic reconstruction through the application of statistical inversion, comprising:
representing unknowns that are associated with points of a reconstruction grid with components of a vector-valued variable,
repeatedly generating a next version of said vector-valued variable by drawing for each component a value from a conditional distribution, and
using the components of a so generated version of said vector-valued variable as said tomographic reconstruction;
wherein:
said components of the vector-valued variable are divided into collections, wherein components in a first collection represent unknowns associated with points of said reconstruction grid that are mutually independent with all points, the unknowns associated with which are represented by components in a second collection, and
for components of different collections, said drawing of values from a conditional distribution is performed in parallel in a computer-implemented process.

3. A method according to claim 1, wherein:
said drawing of values from a conditional distribution is performed in at least one of the following:
parallel threads of a computer-implemented process, parallel cores of a multicore processor, parallel processors of a multiprocessor computing architecture, parallelly operating computers, and
the method comprises, in each of said parallel threads, parallel cores, parallel processors, or parallelly operating computers, allocating and initializing a random number generator independently of other threads, cores, processors, or computers for the drawing of a value from the corresponding conditional distribution.

4. A method according to claim 1, wherein mutually independent points of said reconstruction grid are points for which:
there is no common neighbourhood in which a prior probability density was defined in constructing said tomographic reconstruction, and
there is no common measurement ray that would pass through them.

5. A method according to claim 1, wherein:
tomographic reconstruction is performed from different exposures with multiple views of an examined object, which different exposures have been obtained by rotating a radiation source and a detector facing each other around said object about a vertically oriented rotational axis,
mutually independent points of said reconstruction grid are obtained by selecting, from at least one vertical column of said reconstruction grid, every n:th point, where n is an integer larger than or equal to two.

6. A method according to claim 1, wherein:
tomographic reconstruction is performed from different exposures with multiple views of an examined object, which different exposures have been obtained by rotating a radiation source and a detector facing each other around said object about a vertically oriented rotational axis,
mutually independent collections are obtained by selecting such vertical columns of said reconstruction grid that pass through mutually independent points in a horizontal cross-section of the reconstruction grid.

7. An arrangement for constructing a tomographic reconstruction through the application of statistical inversion, comprising:
a data collection interface configured to obtain a set of measurement data representative of attenuation experienced by electromagnetic waves that propagated through parts of an object to be examined, and
a processor configured to represent unknowns that are associated with points of a reconstruction grid with components of a vector-valued variable, to repeatedly generate a next version of said vector-valued variable by drawing for each component a value from a conditional distribution, and to use the components of a so generated version of said vector-valued variable as said tomographic reconstruction;
wherein:
the processor is configured to divide components of the vector-valued variable into sets, wherein components in a set represent unknowns associated with mutually independent points of said reconstruction grid, and to perform, for at least two components of a set, said drawing of values from a conditional distribution in parallel in a computer-implemented process.

8. An arrangement for constructing a tomographic reconstruction through the application of statistical inversion, comprising:
a data collection interface configured to obtain a set of measurement data representative of attenuation experienced by electromagnetic waves that propagated through parts of an object to be examined, and
a processor configured to represent unknowns that are associated with points of a reconstruction grid with components of a vector-valued variable, to repeatedly generate a next version of said vector-valued variable by drawing for each component a value from a conditional distribution, and to use the components of a so generated version of said vector-valued variable as said tomographic reconstruction;

wherein:

the processor is configured to divide components of the vector-valued variable into collections, wherein components in a first collection represent unknowns associated with points of said reconstruction grid that are mutually independent with all points, the unknowns associated with which are represented by components in a second collection, and to perform, for at least two different collections, said drawing of values from a conditional distribution in parallel in a computer-implemented process.

9. An apparatus according to claim 7, comprising an X-ray imaging section configured to controllably irradiate the object to be examined with X-rays and to detect intensities of X-rays that passed through parts of the object to be examined in order to produce said set of measurement data.

10. An apparatus according to claim 7, comprising user interface means configured to present a graphical image of said tomographic reconstruction to a human user.

11. A non-transitory computer readable storage medium having stored thereon a computer program product for constructing a tomographic reconstruction through the application of statistical inversion, comprising machine-readable instructions that, when executed by a processor, are configured to cause the implementation of:

representing unknowns that are associated with points of a reconstruction grid with components of a vector-valued variable, repeatedly generating a next version of said vector-valued variable by drawing for each component a value from a conditional distribution, and using the components of a so generated version of said vector-valued variable as said tomographic reconstruction;

wherein:

said components of the vector-valued variable are divided into sets, wherein components in a set represent unknowns associated with mutually independent points of said reconstruction grid, and for at least two components of a set, said drawing of values from a conditional distribution is performed in parallel in a computer-implemented process.

12. A non-transitory computer readable storage medium having stored thereon a computer program product for constructing a tomographic reconstruction through the application of statistical inversion, comprising machine-readable instructions that, when executed by a processor, are configured to cause the implementation of:

representing unknowns that are associated with points of a reconstruction grid with components of a vector-valued variable, repeatedly generating a next version of said vector-valued variable by drawing for each component a value from a conditional distribution, and using the components of a so generated version of said vector-valued variable as said tomographic reconstruction;

wherein:

said components of the vector-valued variable are divided into collections, wherein components in a first collection represent unknowns associated with points of said reconstruction grid that are mutually independent with all points, the unknowns associated with which are represented by components in a second collection, and for components of different collections, said drawing of values from a conditional distribution is performed in parallel in a computer-implemented process.

13. A non-transitory computer readable storage medium having stored thereon a computer program product according to claim 11, comprising machine-readable instructions that, when executed by a processor, are configured to cause the implementation of:

performing said drawing of values from a conditional distribution in at least one of the following: parallel threads of a computer-implemented process, parallel cores of a multicore processor, parallel processors of a multiprocessor computing architecture, parallelly operating computers, and in each of said parallel threads, parallel cores, parallel processors, or parallel computers, allocating and initializing a random number generator independently of other threads, cores, processors, or computers for the drawing of a value from the corresponding conditional distribution.

14. A non-transitory computer readable storage medium having stored thereon a computer program product according to claim 12, comprising machine-readable instructions that, when executed by a processor, are configured to cause the implementation of:

performing said drawing of values from a conditional distribution in at least one of the following: parallel threads of a computer-implemented process, parallel cores of a multicore processor, parallel processors of a multiprocessor computing architecture, parallelly operating computers, and in each of said parallel threads, parallel cores, parallel processors, or parallel computers, allocating and initializing a random number generator independently of other threads, cores, processors, or computers for the drawing of a value from the corresponding conditional distribution.

15. A method according to claim 2, wherein:

said drawing of values from a conditional distribution is performed in at least one of the following:

parallel threads of a computer-implemented process, parallel cores of a multicore processor, parallel processors of a multiprocessor computing architecture, parallelly operating computers, and the method comprises, in each of said parallel threads, parallel cores, parallel processors, or parallelly operating computers, allocating and initializing a random number generator independently of other threads, cores, processors, or computers for the drawing of a value from the corresponding conditional distribution.

16. A method according to claim 2, wherein mutually independent points of said reconstruction grid are points for which:

there is no common neighbourhood in which a prior probability density was defined in constructing said tomographic reconstruction, and there is no common measurement ray that would pass through them.

17. A method according to claim 2, wherein:

tomographic reconstruction is performed from different exposures with multiple views of an examined object, which different exposures have been obtained by rotating a radiation source and a detector facing each other around said object about a vertically oriented rotational axis, mutually independent points of said reconstruction grid are obtained by selecting, from at least one vertical column of said reconstruction grid, every n:th point, where n is an integer larger than or equal to two.

18. A method according to claim 2, wherein:
tomographic reconstruction is performed from different exposures with multiple views of an examined object, which different exposures have been obtained by rotating a radiation source and a detector facing each other around said object about a vertically oriented rotational axis,
mutually independent collections are obtained by selecting such vertical columns of said reconstruction grid that pass through mutually independent points in a horizontal cross-section of the reconstruction grid.

19. An apparatus according to claim 8, comprising an X-ray imaging section configured to controllably irradiate the object to be examined with X-rays and to detect intensities of X-rays that passed through parts of the object to be examined in order to produce said set of measurement data.

20. An apparatus according to claim 8, comprising user interface means configured to present a graphical image of said tomographic reconstruction to a human user.

* * * * *